(12) United States Patent
Nobles

(10) Patent No.: US 10,849,615 B2
(45) Date of Patent: Dec. 1, 2020

(54) BALLOON COMPONENT FOR LOCATING A SUTURING DEVICE

(71) Applicant: Heartstitch, Inc., Fountain Valley, CA (US)

(72) Inventor: Anthony Nobles, Fountain Valley, CA (US)

(73) Assignee: HeartStitch, Inc., Fountain Valley, CA (US)

( * ) Notice: Subject to any disclaimer, the term of this patent is extended or adjusted under 35 U.S.C. 154(b) by 150 days.

(21) Appl. No.: 15/844,408

(22) Filed: Dec. 15, 2017

(65) Prior Publication Data

US 2018/0168569 A1 Jun. 21, 2018

Related U.S. Application Data

(60) Provisional application No. 62/434,878, filed on Dec. 15, 2016.

(51) Int. Cl.
| | | |
|---|---|---|
| *A61B 17/04* | (2006.01) | |
| *A61B 17/00* | (2006.01) | |
| *A61B 90/00* | (2016.01) | |
| *A61B 17/06* | (2006.01) | |

(52) U.S. Cl.
CPC ...... *A61B 17/0482* (2013.01); *A61B 17/0057* (2013.01); *A61B 17/0469* (2013.01); *A61B 2017/00557* (2013.01); *A61B 2017/00663* (2013.01); *A61B 2017/00672* (2013.01); *A61B 2017/0472* (2013.01); *A61B 2017/06042* (2013.01); *A61B 2090/036* (2016.02)

(58) Field of Classification Search
CPC ............ A61B 17/0482; A61B 17/0469; A61B 2017/0472; A61B 2017/00557
See application file for complete search history.

(56) References Cited

U.S. PATENT DOCUMENTS

| | | | | |
|---|---|---|---|---|
| 5,486,195 | A * | 1/1996 | Myers | A61B 17/0057 606/191 |
| 5,496,332 | A * | 3/1996 | Sierra | A61B 17/0057 606/139 |
| 5,545,180 | A | 8/1996 | Le | |
| 5,700,273 | A * | 12/1997 | Buelna | A61B 17/04 606/144 |
| 5,709,707 | A | 1/1998 | Lock | |
| 5,830,125 | A * | 11/1998 | Scribner | A61B 17/0057 606/139 |
| 5,836,955 | A * | 11/1998 | Buelna | A61B 17/04 606/148 |
| 5,891,159 | A | 4/1999 | Sherman | |
| 6,117,144 | A * | 9/2000 | Nobles | A61B 17/0057 606/139 |

(Continued)

*Primary Examiner* — Phong Son H Dang
(74) *Attorney, Agent, or Firm* — Fish IP Law, LLP

(57) ABSTRACT

A suturing device uses an inflatable balloon coupled to multiple arms and needles to place sutures at appropriate positions. In preferred embodiments the suturing device includes an elongated body having a working end, a controlling end, and a lumen. The elongated body is coupled to an arm having a distal end with a needle target, which is used to place a suture in an appropriate position relative to the aperture. An inflatable balloon is positioned in an area enclosed by the arm, such that inflating the balloon physically moves a needle towards the needle target.

7 Claims, 4 Drawing Sheets

(56) References Cited

U.S. PATENT DOCUMENTS

| | | | |
|---|---|---|---|
| 6,355,050 B1 * | 3/2002 | Andreas | A61B 17/0469 606/144 |
| 6,358,258 B1 * | 3/2002 | Arcia | A61B 17/0469 606/139 |
| 6,461,366 B1 * | 10/2002 | Seguin | A61B 90/03 606/144 |
| 6,517,553 B2 * | 2/2003 | Klein | A61B 17/0469 606/144 |
| 6,911,034 B2 * | 6/2005 | Nobles | A61B 17/0057 606/144 |
| 6,964,668 B2 * | 11/2005 | Modesitt | A61B 17/0057 606/139 |
| 7,090,686 B2 * | 8/2006 | Nobles | A61B 17/0057 606/139 |
| 7,160,309 B2 * | 1/2007 | Voss | A61B 17/0057 606/144 |
| 7,226,467 B2 * | 6/2007 | Lucatero | A61B 17/0487 606/213 |
| 7,445,626 B2 * | 11/2008 | Songer | A61B 17/0057 606/224 |
| 7,520,883 B2 * | 4/2009 | Manzo | A61B 17/0469 606/139 |
| 7,803,167 B2 * | 9/2010 | Nobles | A61B 17/0625 606/144 |
| 7,837,696 B2 * | 11/2010 | Modesitt | A61B 17/0057 606/139 |
| 7,842,047 B2 * | 11/2010 | Modesitt | A61B 17/0057 606/139 |
| 7,842,048 B2 * | 11/2010 | Ma | A61B 17/0057 606/144 |
| 8,382,797 B2 * | 2/2013 | Khosravi | A61B 17/0057 606/213 |
| 8,419,753 B2 * | 4/2013 | Stafford | A61B 17/0057 606/144 |
| 9,265,488 B2 * | 2/2016 | Galligan | A61B 17/0057 |
| 9,271,708 B2 | 3/2016 | Schltheis | |
| 9,282,953 B2 * | 3/2016 | Pipenhagen | A61B 17/0057 |
| 9,370,353 B2 * | 6/2016 | Fortson | A61B 17/0057 |
| 10,398,418 B2 * | 9/2019 | Palermo | A61B 17/10 |
| 2003/0065345 A1 * | 4/2003 | Weadock | A61B 17/115 606/153 |
| 2004/0068273 A1 | 4/2004 | Fariss | |
| 2005/0004663 A1 * | 1/2005 | Llanos | A61F 2/91 623/1.46 |
| 2005/0070938 A1 * | 3/2005 | Copa | A61B 17/1114 606/153 |
| 2005/0171563 A1 * | 8/2005 | Heinrich | A61B 17/11 606/153 |
| 2005/0251175 A1 * | 11/2005 | Weisenburgh, II | A61B 17/11 606/153 |
| 2006/0100664 A1 * | 5/2006 | Pai | A61B 17/00491 606/214 |
| 2007/0203507 A1 * | 8/2007 | McLaughlin | A61B 17/0625 606/144 |
| 2011/0270282 A1 | 11/2011 | Lemke | |
| 2014/0058440 A1 | 2/2014 | Tegels | |
| 2014/0180311 A1 | 6/2014 | Voss | |

* cited by examiner

BALLOON COMPONENT FOR LOCATING A SUTURING DEVICE

This application claims priority to U.S. Provisional Patent Application No. 62/434,878, filed Dec. 15, 2016, which is incorporated by reference herein in its entirety.

FIELD OF THE INVENTION

The field of the invention is suturing devices.

BACKGROUND

The background description includes information that may be useful in understanding the present invention. It is not an admission that any of the information provided herein is prior art or relevant to the presently claimed invention, or that any publication specifically or implicitly referenced is prior art.

Health practitioners frequently use sutures to close various openings in the body, including cuts, punctures, and incisions. Suturing devices are sometimes uses to assist in such closures, for openings much larger than the operational diameter of the suturing device, it is often hard to properly locate or center the suturing device at the suturing site. Use of an off-center suturing device can decrease the efficiency of the suturing, and even cause damage on the tissues.

U.S. Pat. No. 9,271,708 to Schultheis discloses use of an inflatable balloon for suturing a vessel wall. When the suturing device is placed at the suture location, the balloon is inflated, then a needle pair and suture pair are distally advanced to penetrate through the inflated balloon. One drawback is that since positioning of the needle pair punctures is determined by positioning of the inflated balloon, changes to the size and the shape of the balloon can negatively affect such positioning.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved localization device for centering the suturing device.

SUMMARY OF THE INVENTION

The inventive subject matter provides systems, devices, and methods in which a suturing device sutures large apertures using an inflatable balloon coupled to multiple arms and needles, which place sutures at appropriate positions.

In preferred embodiments, the suturing device includes an elongated body having a working end, a controlling end, and a lumen. The elongated body is coupled to an arm having a distal end with a needle target, which is used to place a suture in an appropriate position relative to the aperture. An inflatable balloon is positioned in an area enclosed by the arm, such that inflating the balloon physically moves a needle towards the needle target.

Another aspect of the invention includes a method for suturing a relatively large aperture with a suturing device having a working end and a controlling end. A suturing device having an elongated body is advanced through the aperture. A balloon disposed on an outer surface of the elongated body is then inflated laterally from the elongated body. The suturing device is then retracted until the inflated balloon contacts the tissue surrounding the aperture. Once the balloon contacts the tissue to be sutured and the suturing device is located at a proper location, an arm and a needle operatively coupled to the elongated body is laterally extended from the elongated body.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
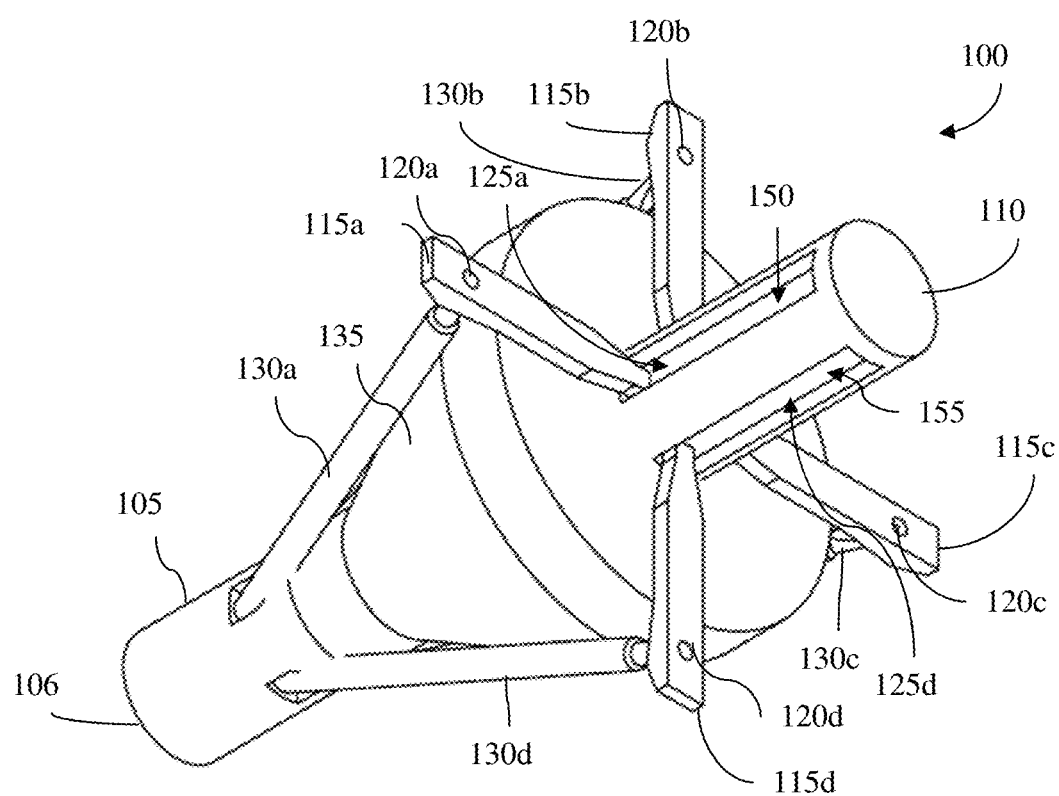
FIG. 1 is a perspective view of a suturing device with an expanded balloon component.

The inventive subject matter provides devices and methods to localize a suturing device at a large aperture of a tissue to effectively suture at or around the large aperture.

While the inventive subject matter is susceptible of various modification and alternative embodiments, certain illustrated embodiments thereof are shown in the drawings and will be described below in detail. It should be understood, however, that there is no intention to limit the invention to the specific form disclosed, but on the contrary, the invention is to cover all modifications, alternative embodiments, and equivalents falling within the scope of the claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified, thus fulfilling the written description of all Markush groups used in the appended claims.

Figure 2:
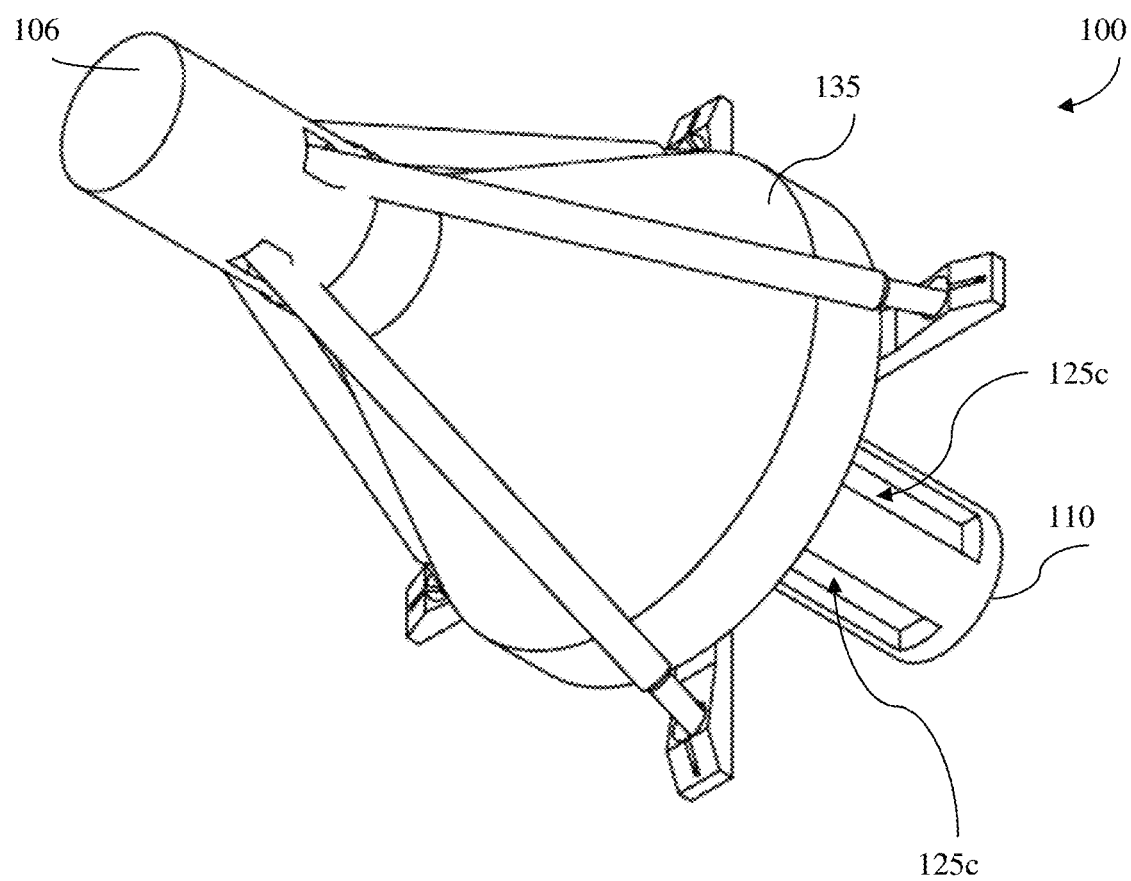
FIG. 2 is another perspective view of the suturing device depicted in FIG. 1.
Figure 3:
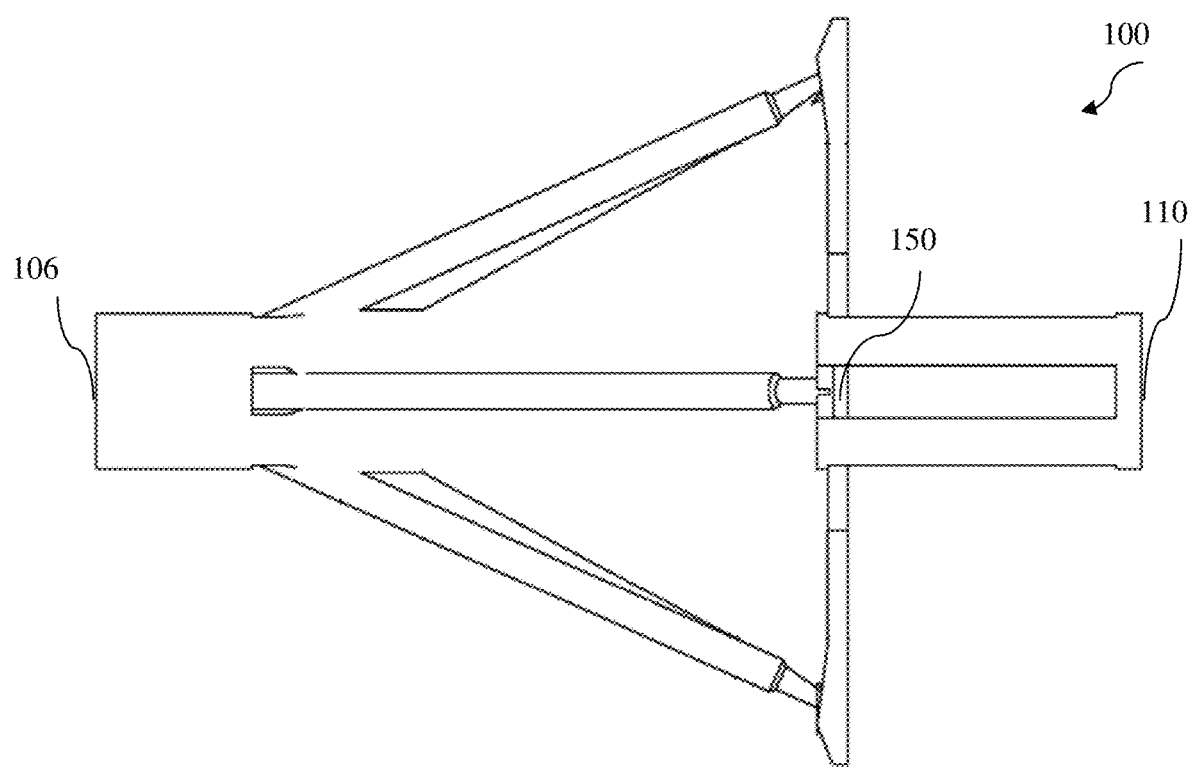
FIG. 3 is a side view of the suturing device of FIG. 1 with an un-inflated balloon component.

One aspect of the inventive subject matter includes a suturing device for suturing large size apertures with a balloon component. FIG. 1 illustrates a perspective view of one exemplary embodiment of the suturing device 100. FIG. 2 illustrates a second perspective view of the exemplary embodiment depicted in FIG. 1 from a different angle. FIG. 3 illustrates a side view of the exemplary embodiment depicted in FIG. 1. The suturing device 100 includes an elongated body 105. The elongated body 105 has a controlling end 106 and a working end 110. The controlling end 106 of the elongated body 105 is the end closest to the user (e.g., a medical provider, a doctor, etc.) when the user operates the suturing device 100. It is preferred that the controlling end 106 is coupled with a controlling means (e.g., a handle, a firing button, a switch, etc.) which improves the controllability of the suturing device 100.

As depicted in FIG. 1, the elongated body 105 is preferably in a cylindrical shape. However, it is contemplated that elongated body 105 can be any shape suitable for inserting into a body cavity, vasculature, or other structure. For example, the elongated body 105 can be cuboid shaped, triangular prism shaped, cone shaped, pyramid shaped, or prism shaped.

It is contemplated that, the elongated body 105 can comprise any suitable material or materials. For example, the elongated body 105 can comprise one or more of plastic materials (e.g., polypropylene, polyethylene, nylon, PVC or PTFE), metal materials (e.g., aluminum, copper, platinum, metal alloys, etc.), silicon, glass fiber, or any suitable combination thereof. In some embodiments, the elongated body 105 is a biocompatible material. For example, the elongated body 105 can comprise one or more of organic fiber-based materials and biodegradable plastics.

The elongated body 105 is coupled to arms 115a, 115b, 115c, and 115d (hereinafter, "arms 115a-d") at the proximal ends of the arms. As depicted, arms 115a-d are hingeably (pivotally) coupled with the elongated body 105 (e.g., at the surface of the elongated body 105, etc.) such that the distal end of arms 115a-d can move laterally away from the elongated body 105. In alternative embodiments, the elongated body 105 includes a lumen 155 which contains a core body 150. Arms 115a-d are hingeably (pivotally) coupled with the core body 150.

As used herein, a lumen 155 is an inside space of a structure. The shape of the lumen 155 depends on the shape of the elongated body 105. For example, the elongated body 105 can a tubular shape, a twisted tubular shape, a cuboid shape, or a triangular prism shape, and the shape of the lumen 155 complements the shape of the elongated body 105. Alternatively, the shape of the lumen 155 can be independent from the shape of the elongated body 105. For example, where the elongated body 105 has tubular shape, the lumen 155 could have a cuboid shape, or vice versa.

In embodiments where arms 115a-d are hingeably (pivotally) coupled with the core body 150, the elongated body 105 can further include one or more openings 125a, 125b, 125c, and 125d (hereinafter, "openings 125a-d") through which arms 115a-d are coupled with the core body 150. Openings 125a-d are preferably in an elongated shape along the length of the elongated body 105. Openings 125a-d are also preferably sized and dimensioned to accommodate arms 115a-d. In preferred embodiments, arms 115a-d are stored in openings 125a-d such that arms 115a-d are substantially parallel to the longitudinal axis of the elongated body 105.

It is also contemplated that the core body 150 and arms 115a-d are slidably coupled inside the lumen 155. When the core body 150 slides toward the working end 110, arms 115a-d slide toward the working end 110 along with the core body 150 and are placed in a closed configuration (i.e., not laterally extended, substantially parallel configuration). When the core body 150 slides toward the controlling end 106, arms 115a-d slide toward the controlling end 106 along with the core body 150, which pivots arms 115a-d to an open configuration (i.e., laterally extended configuration, substantially perpendicular configuration).

Each distal end of arms 115a-d includes a needle target 120a, 120b, 120c, or 120d (hereinafter, "needle targets 120a-d"), respectively, which are configured to at least partially engage with needles 130a, 130b, 130c, and 130d (hereinafter, "needles 130a-d") when arms 115a-d are in an open configuration. Needle targets 120a-d are each coupled with a suture such that needle targets 120a-d can each couple with each respective suture. In this embodiment, needles 130a-d approach the corresponding needle targets 120a-d and hook onto each suture. It is contemplated that the needle targets can have any suitable shape(s) for grabbing or coupling with the sutures. For example, a needle target can be clip shaped, curved pin shaped, hook shaped, or loop shaped.

The elongated body 105 is preferably coupled with an inflatable balloon 135. The inflatable balloon 135 is outside of the elongated body 105 when it is in a deflated configuration (i.e., substantial portion of the inflatable balloon 135 touches the surface of the elongated body 105). The inflatable balloon 135 is configured to be inflated by fluid injection (e.g., air, gas, liquid, gel, etc.) to a size and a shape to defined by an area enclosed by the arms 115a-d and needles 130*a-d* when needles 130*a-d* are in an extended configuration and coupled with arms 115*a-d*.

The inflatable balloon 135 can also be tube-shaped in the deflated configuration and include two open ends such that the inflatable balloon 135 can be stretched over the surface of the elongated body 105 through at least one of the two open ends, such that the inflatable balloon 135 substantially surrounds the elongated body 105. For example, the inflatable balloon 135 can be inserted from the tip of the working ends 110 toward the controlling end 106 so that one open end is placed toward the working end 110 and the other open end is placed toward the controlling end 106. It is highly preferred that the open end at the working end do not overlap or cover any part of openings 125*a-d*, so that the movements of arms 115*a-d* are not physically obstructed or affected in any way by the inflatable balloon 135.

It is also preferred that the inflatable balloon 135 is sealed on the surface of the elongated body 105 at its two open ends so that any fluid (e.g., gas, liquid, etc.) is encapsulated by the inflatable balloon 135. It is contemplated that any suitable type of sealing can be used to prevent leaking of air or other types of fluid (e.g., glue, heat-sealing, etc.).

It is contemplated that the inflatable balloon 135 is configured to be inflated to any desired size to place the suturing device 100 in a desired position through the aperture of the tissue. For example, the inflatable balloon 135 can be inflated such that the largest diameter of the inflated balloon 135 (laterally from the elongated body 105) is at least 5 mm, preferably at least 1 cm, or more preferably at least 1.5 cm.

Any suitable shape of the inflatable balloon 135 is contemplated. Preferably, the inflatable balloon 135 has a larger diameter at the working end than at the controlling end when fully inflated. For example, the inflatable balloon 135 can be cone shaped when fully inflated with the larger diameter at the working end so that the inflated balloon 135 cannot pass through the aperture toward the controlling end side (e.g., anchoring the suturing device 100). In another example, the inflatable balloon 135 can be pyramid shaped, ellipsoid shaped, hemisphere shaped, torus shaped (i.e. a ring), octahedron shaped, or wedge shaped.

It is contemplated that any suitable types of materials can be used to construct the inflatable balloon 135. The inflatable balloon 135 preferably comprises one or more of plastic materials (e.g., polypropylene, polyethylene, nylon, PVC, and/or PTFE), rubbers, vinyl, silicon, or fiber (e.g., cotton, synthetic fiber, etc.).

Figure 4A:
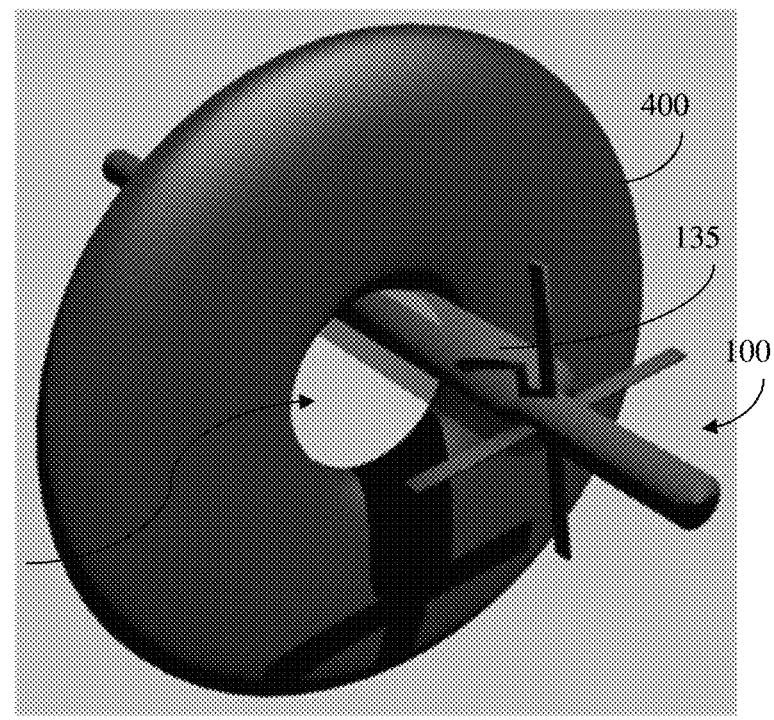
FIG. 4A is a perspective view of the suturing device of FIG. 1 with the un-inflated balloon component located at a tissue.
Figure 4B:
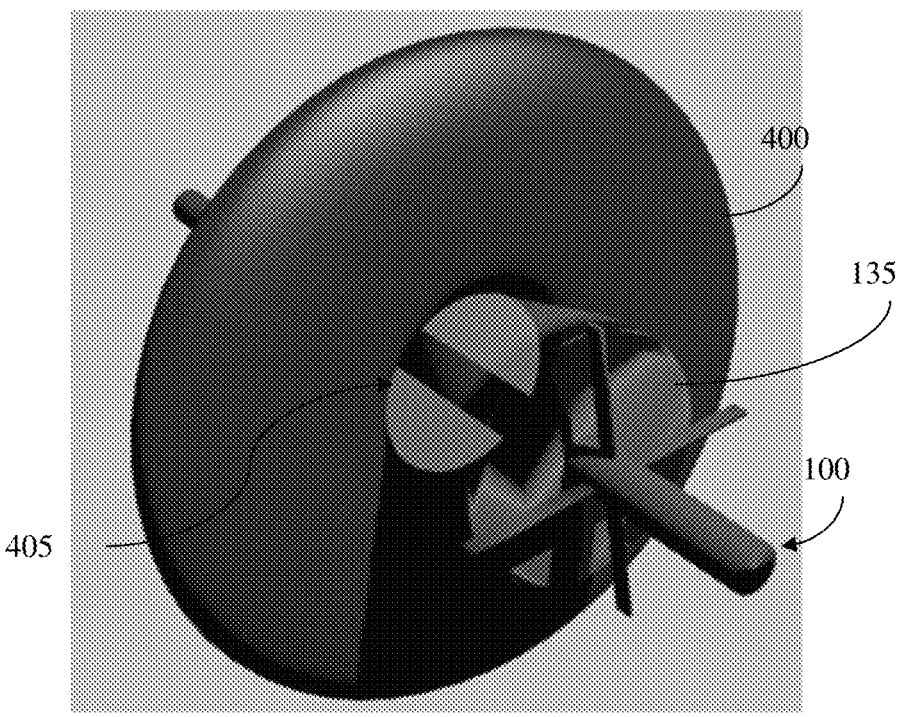
FIG. 4B is a perspective view of the suturing device of FIG. 1 with the inflated balloon component located at the tissue.

The inventive subject matter also includes a method for suturing a large size aperture with a suturing device 100 described in FIGS. 1-3. The method begins with a step of advancing a suturing device 100 having an elongated body 105 through the aperture 405. FIGS. 4A-B illustrate an exemplary embodiment in which the working end of the suturing device 100 passes through the aperture 405 of the tissue 400. In FIG. 4A, the user moves the suturing device 100 so that the distal end of the suturing device including the inflatable balloon 135 passes through the aperture 405. In FIG. 4B, the method continues with a step of inflating the inflatable balloon 135 laterally from the elongated body. The inflatable balloon 135 is, when inflated, sized and dimensioned to be placed in an area enclosed (or surrounded) by the first arm and the first needle, wherein the first needle is coupled with the first needle target. After the balloon 135 is inflated, the suturing device 100 retracts toward the direction of the controlling end such that the balloon 135 contacts a tissue 400 surrounding the aperture 405 and adjusts the localization of the suturing device 100 in a desired way. The arms are then laterally and outwardly extended toward the needle target.

In a preferred embodiment, the method also comprises a step of engaging the balloon 135 on the elongated body by sliding the elongated body through the first open end and the second open end of the balloon 135 before the suturing step begins. When the suturing steps are completed, the volume of the inflated balloon 135 can be reduced by removing fluid from the lumen of the inflatable balloon 135, thereby allowing the suturing device 100 to be removed entirely from the suturing area (e.g., incisions, apertures, etc.). The inflatable balloon 135 can also be re-inflated and reused by inserting fluid into the lumen of the inflatable balloon 135. Alternatively, the inflatable balloon 135 can be removed by slipping away from the elongated body after use and disposing of it.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for suturing a large size aperture with a suturing device having a working end and a controlling end, comprising steps of: advancing a suturing device having an elongated body through the aperture, wherein the elongated body comprises a proximal and a distal end; inflating a balloon laterally from the distal end of the elongated body; retracting the suturing device until the balloon contacts a tissue surrounding the apertures; extending a first arm with a proximal and a distal end laterally from the elongated body, wherein the first arm is positioned distal of the balloon and the proximal end of the first arm is coupled to a core body slidably disposed inside a lumen of the elongated body through the opening; and advancing a first needle laterally towards the distal end.

2. The method of claim 1, wherein the balloon further comprises a first open end, a second open end, and a lumen, and the method further comprises engaging the balloon on the elongated body by sliding the elongated body through the first open end and the second open end of the balloon.

3. The method of claim 2, further comprising a step of sealing the first open end and the second open end to an outer surface of the elongated body.

4. The method of claim 1, wherein the extending the first arm comprises sliding the core body toward the controlling end.

5. The method of claim 1, wherein the balloon is fluidly coupled with a lumen of the elongated body, and inflating the balloon comprises inserting fluid from the lumen of the elongated body into the balloon.

6. The method of claim 5, further comprising a step of deflating the balloon by removing the fluid from the balloon to the lumen of the elongated body.

7. The method of claim 1, further comprising localizing the suturing device laterally after the balloon contacts a tissue surrounding the aperture.

\* \* \* \* \*